(12) United States Patent
Nogueiras Nieto et al.

(10) Patent No.: US 10,688,050 B1
(45) Date of Patent: Jun. 23, 2020

(54) PHARMACEUTICAL COMPOSITION COMPRISING IBRUTINIB

(71) Applicant: Synthon B.V., Nijmegen (NL)

(72) Inventors: Luis Nogueiras Nieto, Sant Boi de Llobregat (ES); Sara Fradera Gelabert, Sant Boi de Llobregat (ES); Lisardo Alvarez Fernandez, Sant Boi de Llobregat (ES); Rohit Kumar, Sant Boi de Llobregat (ES)

(73) Assignee: Synthon B.V., Nijmegen (NL)

(*) Notice: Subject to any disclaimer, the term of this patent is extended or adjusted under 35 U.S.C. 154(b) by 26 days.

(21) Appl. No.: 16/229,282

(22) Filed: Dec. 21, 2018

(51) Int. Cl.
*A61K 9/20* (2006.01)
*A61P 35/02* (2006.01)
*A61K 31/519* (2006.01)

(52) U.S. Cl.
CPC .......... *A61K 9/2018* (2013.01); *A61K 9/2027* (2013.01); *A61K 9/2054* (2013.01); *A61K 9/2095* (2013.01); *A61K 31/519* (2013.01); *A61P 35/02* (2018.01)

(58) Field of Classification Search
None
See application file for complete search history.

(56) References Cited

U.S. PATENT DOCUMENTS

| | | | |
|---|---|---|---|
| 9,665,857 | B2 | 5/2017 | Chong et al. |
| 10,010,507 | B1 * | 7/2018 | Chong ............... A61K 9/2009 |
| 10,213,386 | B2 | 2/2019 | Chong et al. |
| 2016/0287694 | A1 | 10/2016 | Gupta et al. |
| 2019/0224204 | A1 | 7/2019 | Malhotra et al. |

FOREIGN PATENT DOCUMENTS

| | | | | |
|---|---|---|---|---|
| CN | 103923084 | | 7/2014 | |
| CN | 105294696 | | 2/2016 | |
| CN | 105646484 | | 6/2016 | |
| CN | 105646498 | | 6/2016 | |
| CN | 105646499 | | 6/2016 | |
| CN | 106117214 | | 11/2016 | |
| CN | 107286163 | | 10/2017 | |
| EP | 3243824 | | 11/2017 | |
| WO | WO2008039218 | | 4/2008 | |
| WO | WO2013184572 | | 12/2013 | |
| WO | WO-2014004707 | A1 * | 1/2014 | ............ A61K 45/06 |
| WO | WO2015081180 | | 6/2015 | |
| WO | WO2015145415 | | 10/2015 | |
| WO | WO2016025720 | | 2/2016 | |
| WO | WO2016079216 | | 5/2016 | |
| WO | 2016141068 | | 9/2016 | |
| WO | WO2016139588 | | 9/2016 | |
| WO | 2016164404 | | 10/2016 | |
| WO | WO2016160598 | | 10/2016 | |
| WO | WO2017029586 | | 2/2017 | |
| WO | WO2017085628 | | 5/2017 | |
| WO | WO-2017125423 | A1 * | 7/2017 | ........... A61K 9/2013 |
| WO | WO-2017125424 | A1 * | 7/2017 | ........... A61K 9/2013 |
| WO | WO2018000250 | | 1/2018 | |

OTHER PUBLICATIONS

Zvonicek et al., Crystal Growth & Design (2018), 18(3), pp. 1315-1326.*

* cited by examiner

*Primary Examiner* — Brian J Davis
(74) *Attorney, Agent, or Firm* — Buscher Patent PLLC

(57) ABSTRACT

The present invention relates to a tablet composition comprising ibrutinib and one or more pharmaceutically acceptable excipients, characterized in that:
  ibrutinib is form C, having characteristic peaks in the X-ray powder diffraction pattern at the following 2 theta (±0.2) angles: 6.9°, 18.2°, 19.2°, 19.6° and 23.0°, measured using a Cu Kα radiation, and
  the composition is free of surfactant, and
  the composition exhibits a dissolution rate of at least 65% in 20 minutes when tested in 900 ml 0.01 N hydrochloric acid pH 2.0 (+1% Tween 20) at 37° C., 75 rpm and/or in 900 ml phosphate buffer pH 6.8 (+3% Tween 20) at 37° C., 75 rpm in a USP apparatus II.

The invention further relates to the use of said composition as a medicament, particularly in the treatment of chronic lymphocytic leukaemia (CLL), mantle cell lymphoma (MCL) and Waldenström's macroglobulinaemia (WM).

17 Claims, 2 Drawing Sheets

PHARMACEUTICAL COMPOSITION COMPRISING IBRUTINIB

BACKGROUND OF THE PRESENT INVENTION

Ibrutinib, chemically 1-[(3R)-3-[4-amino-3-(4-phenoxyphenyl)-1H-pyrazolo[3,4-d]pyrimidin-1-yl]piperidin-1-yl]prop-2-en-1-one of formula (I),

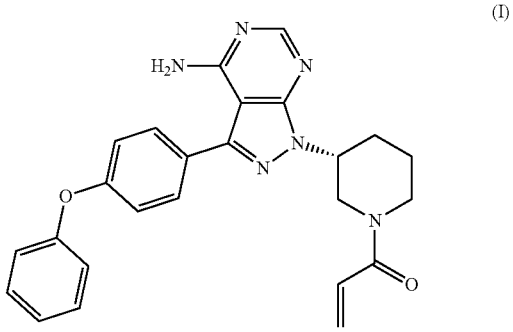 [SMILES: C=CC(=O)N1CCC[C@@H](n2nc(-c3ccc(Oc4ccccc4)cc3)c3c(N)ncnc32)C1]

is a pharmaceutically active compound. It is used for the treatment of chronic lymphocytic leukaemia (CLL) in previously untreated patients and in patients who have received at least one previous treatment. It is also used for the treatment of mantle cell lymphoma (MCL) in patients whose disease does not respond to or has come back after previous treatment and to treat Waldenström's macroglobulinaemia (WM), also known as lymphoplasmacytic lymphoma, in patients who have had previous treatment or who cannot have chemo immunotherapy.

Ibrutinib is marketed by Janssen/Pharmacyclics under the brand name Imbruvica® and is disclosed in WO2008039218. Imbruvica® was initially only supplied as hard capsule in one strength: 140 mg. Patients take either 3 or 4 capsules once daily, depending on the disease to be treated. Recently, the FDA approved a new tablet formulation of Imbruvica®. The tablet is available in the strengths 140, 280, 420 and 560 mg and thus reduces pill burden for patients.

Several crystalline forms of ibrutinib are described in literature. WO2013184572 discloses crystalline forms A, B and C and solvated forms D (methyl isobutyl ketone solvate), E (toluene solvate) and F (methanol solvate). The marketed product Imbruvica®, both capsule and tablet formulation, contains crystalline ibrutinib form A. Other forms of ibrutinib are disclosed in CN103923084, WO2015081180, WO2015145415, WO2016025720, WO2016079216, CN105294696, CN105646484, CN105646499, CN105646498, WO2016160598, WO2016139588, WO2017029586, CN106117214, WO2017085628, CN107286163, EP3243824 and WO2018000250. Some of the described forms do contain unwanted solvents. Moreover, it was experienced in our laboratory that some of these forms are rather unstable.

Ibrutinib is a BCS class II compound, exhibiting low solubility and high permeability.

Both capsule and tablet composition of Imbruvica® contain a considerable amount of the anionic surfactant sodium lauryl sulphate (SLS). It is known that this compound may give rise to irritation of the gastrointestinal tract.

It would be desirable to have a tablet composition comprising ibrutinib that exhibits adequate dissolution and is free of surfactant. The composition should be stable, suitable for production on commercial scale and bioequivalent to Imbruvica®.

BRIEF DESCRIPTION OF THE PRESENT INVENTION

The present invention provides a tablet composition comprising ibrutinib and one or more pharmaceutically acceptable excipients, characterized in that:
ibrutinib is form C, having characteristic peaks in the X-ray powder diffraction pattern at the following 2 theta (±0.2) angles: 6.9°, 18.2°, 19.2°, 19.6° and 23.0°, measured using a Cu Kα radiation, and
the composition is free of surfactant, and
the composition exhibits a dissolution rate of at least 65% in 20 minutes when tested in 900 ml 0.01 N hydrochloric acid pH 2.0 (+1% Tween 20) at 37° C., 75 rpm and/or in 900 ml phosphate buffer pH 6.8 (+3% Tween 20) at 37° C., 75 rpm in a USP apparatus II.

It also provides a process for preparing the tablet composition comprising a granulation step.

Said pharmaceutical composition may be used as a medicament, particularly in the treatment of chronic lymphocytic leukaemia (CLL), mantle cell lymphoma (MCL) and Waldenström's macroglobulinaemia (WM).

DETAILED DESCRIPTION OF THE PRESENT INVENTION

Imbruvica® contains the crystalline ibrutinib form A as disclosed in WO2013184572. Ibrutinib from A is a very stable compound, but being a BCS class II compound, it exhibits low aqueous solubility which affects dissolution behavior. The compound is slightly soluble at pH 1.2 and practically insoluble in the pH range from 3 to 8.

Other forms of ibrutinib have been disclosed in the prior art. Some of these forms are solvated forms of ibrutinib and some of them do contain unwanted (e.g. toxic) solvents. Moreover, some of the forms as disclosed in the prior art are rather unstable.

Figure 1:
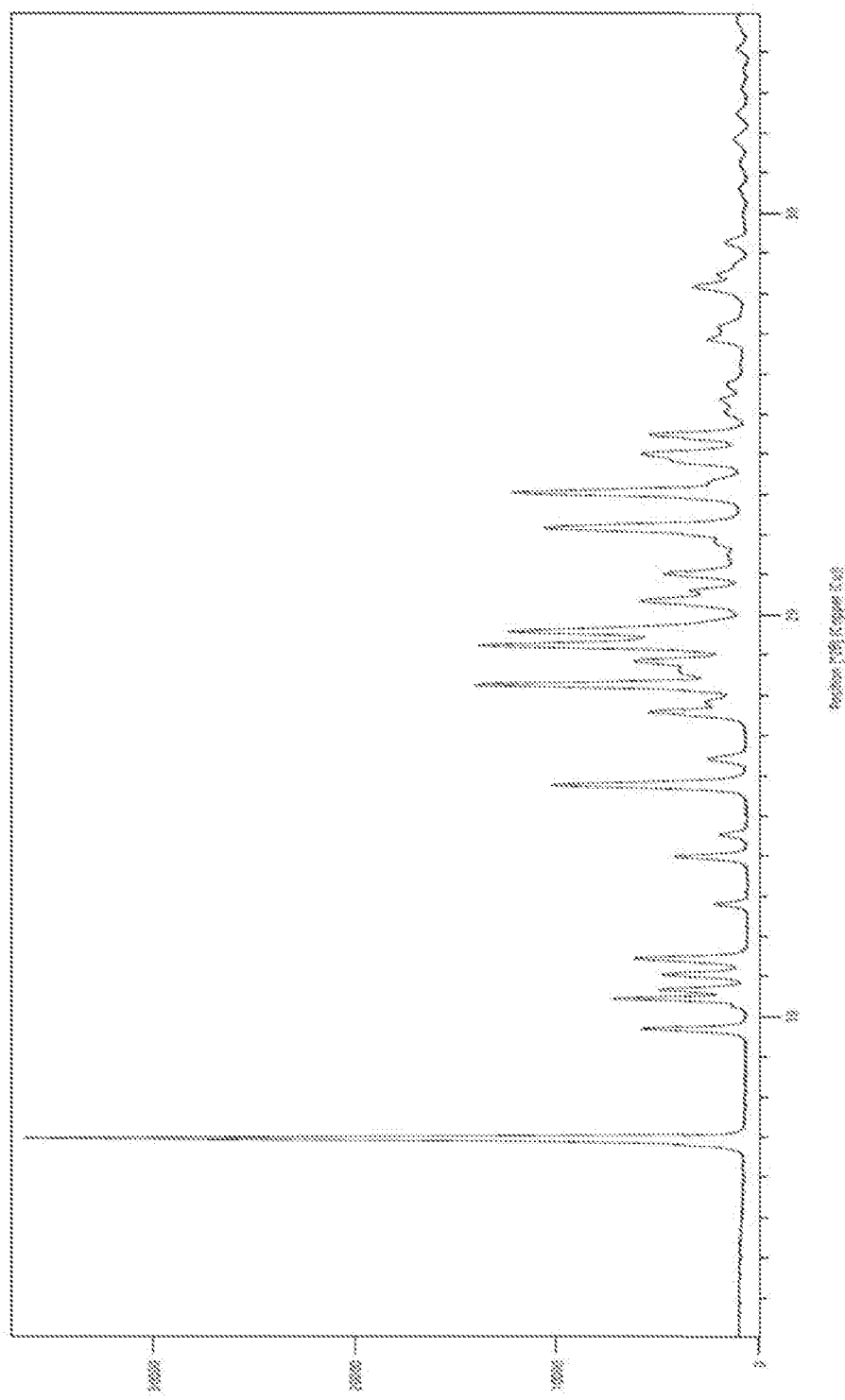
FIG. 1 shows the full XRPD pattern of ibrutinib form C. For measurement conditions see the Examples section.

WO2013184572 discloses, besides ibrutinib form A, crystalline forms B and C and solvated forms D (methyl isobutyl ketone solvate), E (toluene solvate) and F (methanol solvate). The XRPD pattern of ibrutinib form C is shown in FIG. 1. This crystalline form is less stable than ibrutinib form A, but exhibits a significantly higher aqueous solubility.

Both capsule and tablet composition of Imbruvica® contain a considerable amount of the anionic surfactant sodium lauryl sulphate (SLS). It is known that this compound, like some other surfactants, may give rise to irritation of the gastrointestinal tract. It would thus be advantageous to have a pharmaceutical composition comprising ibrutinib that is free of surfactant.

It was surprisingly found by the present inventors that a tablet composition exhibiting a similar dissolution profile as Imbruvia® and which is completely free of surfactant, can be obtained by using ibrutinib form C. The tablet composition of the present invention is very stable and even after storage at elevated temperature or increased relative humidity, ibrutinib form C in the composition does not convert into ibrutinib form A or any other crystalline form of ibrutinib. The tablet is prepared by a robust and cost effective process and is bioequivalent to Imbruvica®.

The present invention thus provides a tablet composition comprising ibrutinib and one or more pharmaceutically acceptable excipients, characterized in that:
- ibrutinib is form C, having characteristic peaks in the X-ray powder diffraction pattern at the following 2 theta (±0.2) angles: 6.9°, 18.2°, 19.2°, 19.6° and 23.0°, measured using a Cu Kα radiation, and
- the composition is free of surfactant, and
- the composition exhibits a dissolution rate of at least 65% in 20 minutes when tested in 900 ml 0.01 N hydrochloric acid pH 2.0 (+1% Tween 20) at 37° C., 75 rpm and/or in 900 ml phosphate buffer pH 6.8 (+3% Tween 20) at 37° C., 75 rpm in a USP apparatus II.

The XRPD pattern of ibrutinib form C may further comprise characteristic peaks at the following 2 theta (±0.2) angles: 15.7°, 17.5°, 20.3°, 22.1° and 24.0°, measured using a Cu Kα radiation. The XRPD pattern of ibrutinib form C is shown in FIG. 1.

The tablet composition in accordance with the present invention is free of surfactant and does thus not contain SLS or any other surfactant. Main advantage thereof is that irritation, of e.g. gastrointestinal tract, is prevented.

Ibrutinib form C is present in the tablet composition of the present invention in an amount from 60 to 80% w/w relative to the total weight of the tablet. Most preferably, ibrutinib form C is present in the tablet composition in an amount from 65 to 75% w/w relative to the total weight of the tablet.

The tablet compositions according to the present invention display dissolution behavior typical for immediate-release formulations. The compositions of the present invention exhibit a dissolution rate of at least 65% in 20 minutes when tested in 900 ml 0.01 N hydrochloric acid pH 2.0 (+1% Tween 20) at 37° C., 75 rpm and/or in 900 ml phosphate buffer pH 6.8 (+3% Tween 20) at 37° C., 75 rpm in a USP apparatus II.

The tablet compositions according to the present invention comprise, besides ibrutinib form C, one or more pharmaceutically acceptable excipients. The excipients to be used in accordance with the present invention are well-known and are those excipients which are conventionally used by the person skilled in the art. The pharmaceutically acceptable excipients are chosen from one or more diluents, binders, disintegrants, glidants or lubricants.

The pharmaceutical composition according to the present invention comprises preferably 10-30% w/w of one or more diluents, 0-5% w/w of one or more binders, 2-15% w/w of one or more disintegrants, 0.25-1.0% w/w of one or more glidants and 0.25-2.0% w/w of one or more lubricants, all relative to the total tablet weight.

The diluent to be used in accordance with the present invention may be any diluent known to a person of ordinary skill in the art. Particularly, the diluent to be used in accordance with the present invention is an inorganic diluent, polysaccharide, mono- or disaccharide or sugar alcohol. Lactose and microcrystalline cellulose are particularly preferred diluents.

In another embodiment of the present invention, the diluent to be used in accordance with the present invention is a basifying excipient, e.g. metal carbonate or bicarbonate. This type of diluent may decrease the dissolution rate of the tablet comprising ibrutinib by way of its basic character. A particularly preferred basifying excipient is sodium bicarbonate.

The diluent to be used in accordance with the present invention may contain lactose, microcrystalline cellulose, a basifying excipient or mixtures thereof.

The binder to be used in accordance with the present invention may be any binder known to a person of ordinary skill in the art. Suitable binders are selected from the group consisting of sodium carboxymethylcellulose, polyvinyl pyrrolidone (PVP), copovidone, polyvinyl pyrrolidone-vinyl acetate (PVP/VA) copolymer, hydroxypropylcellulose, hydroxypropyl methylcellulose or ethyl cellulose. PVP is a particularly preferred binder.

The disintegrant to be used in accordance with the present invention may be any disintegrant known to a person of ordinary skill in the art. Suitable disintegrants to be used in accordance with the present invention are selected from the group consisting of croscarmellose sodium, crospovidone, low-substituted hydroxypropylcellulose or sodium starch glycolate. Croscarmellose sodium is a particularly preferred disintegrant.

The glidant to be used in accordance with the present invention may be any glidant known to a person of ordinary skill in the art. Colloidal silicon dioxide is a particularly preferred glidant.

The lubricant to be used in accordance with the present invention may be any lubricant known to a person of ordinary skill in the art. Magnesium stearate is a particularly preferred lubricant.

The tablets may be optionally further coated by a film-coat. The coating serves generally for cosmetic purposes. The coating material typically has no influence on the release rate, except of an inherent short initial delay in dissolution due to the time necessary to dissolve the coat. The coating may be selected from amongst one or more of those suitable coating materials known in the art.

The coating may be performed by applying one or more film forming polymers, with or without other pharmaceutically inert excipients, as a solution/suspension. Coating is done using any conventional coating technique known in the art, such as spray coating in a conventional coating pan or fluidized bed processor; or dip coating.

The tablet composition according to the present invention is packaged in primary packaging material, e.g. blisters and bottles. The tablet composition of the present invention is preferably packaged in capped bottles. HDPE bottles are particularly preferred. The capped bottles may comprise means to absorb water by having a cap containing desiccant, e.g. silica gel.

The pharmaceutical composition of the present invention exhibits excellent long term stability. After storage of the composition for 3 months at 40° C./75% RH, XRPD analysis showed that ibrutinib was kept in form C and did not convert into any other polymorphic form. Moreover, the pharmaceutical composition of the present invention is very suitable for production on commercial scale making use of equipment and techniques commonly used in industry.

The present invention further provides a process to prepare a tablet composition comprising ibrutinib form C and one or more pharmaceutically acceptable excipients comprising a granulation step. The granulation processes applied are simple and cost effective and include a standard wet or dry granulation technique.

The wet granulation process is performed with a granulation solvent selected from the group consisting of water, acetone, ethanol, isopropanol or a mixture thereof.

Preferably, the process to prepare the tablet composition of the present invention comprises a dry granulation step. The dry granulation step is conducted by either slugging or roller compaction. The advantage of the dry granulation over the process of wet granulation is that it does not use any organic solvents or water. The risk of stability issues is minimized in this way, especially when active pharmaceutical ingredients are used that are prone to (polymorphic) conversion.

The tablet prepared by applying the step of dry granulation comprises, besides ibrutinib form C, one or more pharmaceutically acceptable binders, diluents, disintegrants, glidants or lubricants. Preferably, the tablet prepared by using the step of dry granulation comprises ibrutinib form C, lactose, microcrystalline cellulose, polyvinylpyrrolidone (PVP), croscarmellose sodium, silicon dioxide and magnesium stearate.

The grade of lactose used in the dry granulation process comprising ibrutinib is preferably lactose anhydrous. This grade of lactose has good compression properties and may increase the hardness of the tablets. The final blend comprising granules with lactose anhydrous exhibits good tabletability and does not give rise to any sticking issues.

The binder is added to the intragranular phase. The disintegrant may be added as intragranular component or it may be divided over the intragranular and extragranular phase. In a preferred embodiment, the disintegrant is added partially to the intragranular phase and partially to the extragranular phase. The diluent may be added as intragranular component or it may be divided over the intragranular and extragranular phase. In a preferred embodiment, the diluent is added partially to the intragranular phase and partially to the extragranular phase. The lubricant may be added as extragranular component or it may be divided over the intragranular and extragranular phase. In a preferred embodiment, the lubricant is added partially to the intragranular phase and partially to the extragranular phase. The glidant may be added as intragranular component or it may be divided over the intragranular and extragranular phase. In a preferred embodiment, the glidant is added to the intragranular phase.

The tablet composition in accordance with the present invention may be used as a medicament. The composition typically may be used in the treatment of chronic lymphocytic leukaemia (CLL), mantle cell lymphoma (MCL) and Waldenström's macroglobulinaemia (WM).

The following examples are intended to illustrate the scope of the present invention but not to limit it thereto.

EXAMPLES

The full XRPD pattern of ibrutinib form C of FIG. 1 was obtained using a Bruker-AXS D8 Vario diffractometer with θ/2θ geometry (reflection mode), equipped with a Lynxeye detector and applying the following measurement conditions:
Start angle (2θ): 2.0°
End angle (2θ): 35.0°
Scan step width: 0.02°
Scan step time: between 0.2-2.0 seconds
Radiation type: Cu
Radiation wavelengths: 1.5406 Å (Kα1), primary monochromator used
Exit slit: 6.0 mm
Focus slit: 0.2 mm
Divergence slit: Variable (V20)
Antiscatter slit: 11.8 mm
Receiving slit: 20.7 mm Example 1: Pharmaceutical Composition Comprising Ibrutinib Form C The film-coated tablets comprising ibrutinib form C were prepared by the process of dry granulation and have the composition as given in table 1.

TABLE 1

| Component | Ibrutinib tablet composition | |
|---|---|---|
| | mg/tablet | % |
| Intragranular components | | |
| Ibrutinib form C | 560.0 | 70.0 |
| Lactose anhydrous | 112.0 | 14.0 |
| PVP K-25 | 16.0 | 2.0 |
| Croscarmellose sodium | 40.0 | 5.0 |
| Magnesium stearate | 4.0 | 0.5 |
| Extragranular components | | |
| Microcrystalline cellulose | 44.0 | 5.5 |
| Croscarmellose sodium | 16.0 | 2.0 |
| Colloidal silicon dioxide | 4.0 | 0.5 |
| Magnesium stearate | 4.0 | 0.5 |
| Total core tablet weight | 800.0 | 100.0 |

Figure 2:
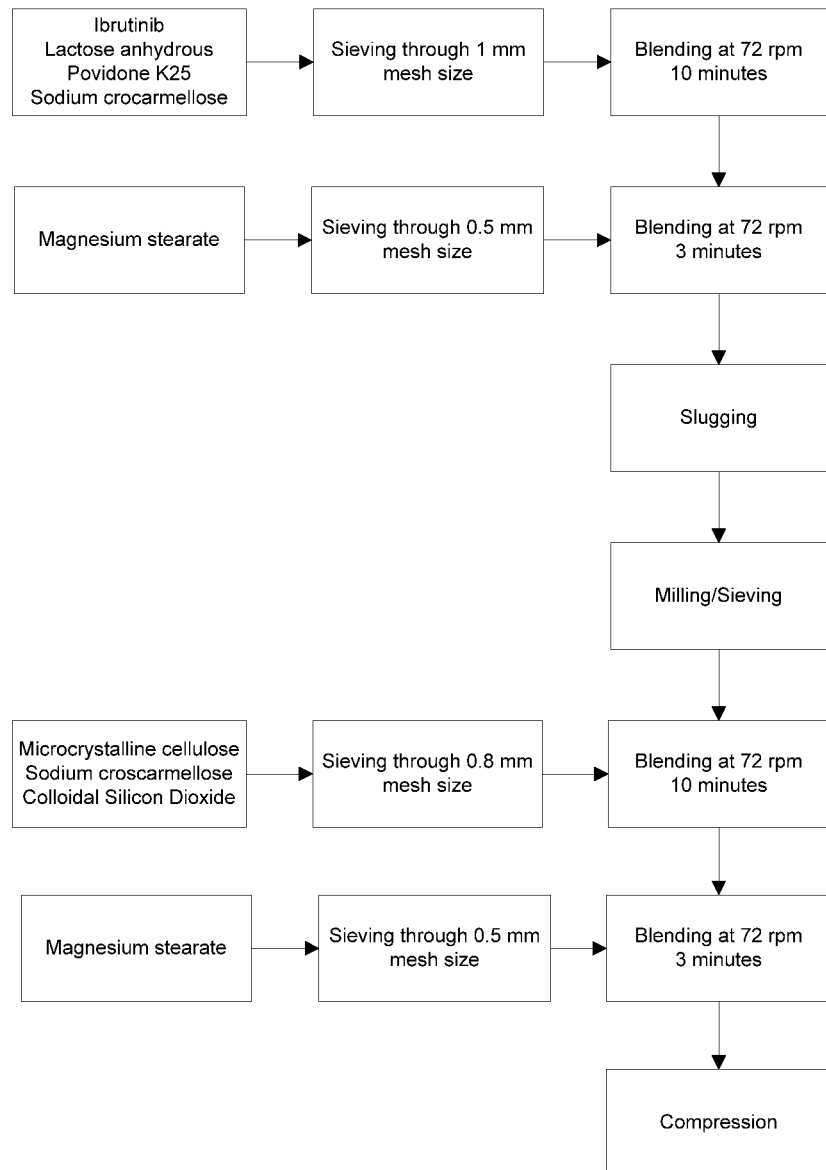
FIG. 2 shows the flow chart of the process of dry granulation applied to prepare the tablets of Example 1.

The tablets were prepared by the dry granulation process as depicted in the flowchart of FIG. 2.

The tablets were packed in Alu/Alu blisters and in HDPE bottles, comprising desiccant in the cap.

XRPD analysis performed after storing the tablets for 3 months at 40° C./75% RH showed that ibrutinib is present in form C; no conversion into any other polymorphic form of ibrutinib was observed.

The tablets obtained, exhibited a dissolution rate of at least 65% in 20 minutes when tested in 900 ml 0.01 N hydrochloric acid pH 2.0 (+1% Tween 20) at 37° C., 75 rpm or in 900 ml phosphate buffer pH 6.8 (+3% Tween 20) at 37° C., 75 rpm in a USP apparatus II. The dissolution profiles of the tablets match the profiles of Imbruvica®.

The invention claimed is:

1. A tablet composition comprising ibrutinib and one or more pharmaceutically acceptable excipients, wherein:
    ibrutinib is form C, having characteristic peaks in the X-ray powder diffraction pattern at the following 2 theta (±0.2) angles: 6.9°, 18.2°, 19.2°, 19.6° and 23.0°, measured using a Cu Kα radiation, and
    said ibrutinib from C is present in an amount from 60 to 80% w/w relative to the total weight of the tablet, and the composition is free of surfactant, and
    the composition exhibits a dissolution rate of at least 65% in 20 minutes when tested in 900 ml 0.01 N hydrochloric acid pH 2.0 (+1% polysorbate 20) at 37° C., 75 rpm and/or in 900 ml phosphate buffer pH 6.8 (+3% polysorbate 20) at 37° C., 75 rpm in a USP apparatus II.

2. The tablet composition according to claim 1, wherein the pharmaceutically acceptable excipients are chosen from one or more diluents, binders, disintegrants, glidants or lubricants.

3. The tablet composition according to claim 2, wherein the diluent contains lactose, microcrystalline cellulose, a basifying excipient, or mixtures thereof.

4. The tablet composition according to claim 2, wherein the tablet comprises 10-30% w/w of one or more diluents, 0-5% w/w of one or more binders, and 2-15% w/w of one or more disintegrants, all relative to the total tablet weight.

5. The tablet composition according to claim 4, wherein said one or more diluents are selected from lactose, microcrystalline cellulose, and mixtures thereof.

6. The tablet composition according to claim 4, wherein the one or more binders are selected from the group consisting of sodium carboxymethylcellulose, polyvinyl pyrrolidone (PVP), copovidone, polyvinyl pyrrolidone-vinyl acetate (PVP/VA) copolymer, hydroxypropylcellulose, hydroxypropyl methylcellulose, and ethyl cellulose.

7. The tablet composition according to claim 4, wherein the one or more disintegrants are selected from the group consisting of croscarmellose sodium, crospovidone, low-substituted hydroxypropylcellulose, and sodium starch glycolate.

8. The tablet composition according to claim 4, which further comprises 0.25-1.0% w/w of one or more glidants and 0.25-2.0% w/w of one or more lubricants, all relative to the total tablet weight.

9. The tablet composition according to claim 1, which was made by a process that comprises granulating said ibrutinib form C and at least one of said pharmaceutically acceptable excipients to form ibrutinib granules.

10. The tablet composition according to claim 9, wherein the granulating is a dry granulation step.

11. The tablet composition according to claim 10, wherein the process further comprises blending the ibrutinib granules with one or more additional excipients and compressing the resulting mixture into tablets.

12. A method for treating chronic lymphocytic leukaemia (CLL), mantle cell lymphoma (MCL) or Waldenstrom's macroglobulinaemia (WM), which comprises administering to a patient in need thereof the tablet composition according to claim 1.

13. The tablet composition according to claim 11, wherein said ibrutinib is granulated with pharmaceutically acceptable excipients comprising a binder, a diluent, and a disintegrant.

14. The tablet composition according to claim 13, wherein said binder is polyvinyl pyrrolidone (PVP) and said diluent is lactose.

15. The tablet composition according to claim 13, wherein said one or more additional excipients that are blended with the ibrutinib granules comprise a diluent, a lubricant, and a disintegrant.

16. The tablet composition according to claim 15, wherein the intragranular diluent is lactose and the extragranular diluent is microcrystalline cellulose.

17. The tablet composition according to claim 16, wherein the intragranular and extragranular disintegrant is croscarmellose sodium.

* * * * *